United States Patent [19]
Matsuno et al.

[11] Patent Number: 6,124,466
[45] Date of Patent: Sep. 26, 2000

[54] NITROISOUREA DERIVATIVE

[75] Inventors: Hirozumi Matsuno; Kiyoshi Arai; Takeshi Oura; Kenji Kodaka, all of Chiba-ken, Japan

[73] Assignee: Mitsui Chemicals, Inc., Japan

[21] Appl. No.: 09/357,001

[22] Filed: Jul. 19, 1999

[30] Foreign Application Priority Data

Jul. 24, 1998 [JP] Japan ................................. 10-209739
Jul. 31, 1998 [JP] Japan ................................. 10-217974

[51] Int. Cl.$^7$ ..................... C07D 307/14; C07D 277/28; C07D 213/53; C07C 275/70
[52] U.S. Cl. .................... 546/332; 548/205; 549/495; 558/8
[58] Field of Search ........................ 546/332; 548/205; 549/495; 558/8

[56] References Cited

U.S. PATENT DOCUMENTS 5,034,404  7/1991  Unene et al. ........................ 548/205 X
5,434,181  7/1995  Kodaka et al. ..................... 549/495 X

FOREIGN PATENT DOCUMENTS 97 00867  1/1997  WIPO .

OTHER PUBLICATIONS

N. Heyboer et al., "Note on the Conversion of the Amino Group of Amino Acids into the Nitroguanidino Group", Recueil Des Travaux Chimiques Des Pays–Bas, vol. 81, No. 1, Jan. 1, 1962, pp. 69–72.

*Primary Examiner*—Michael G. Ambrose
*Attorney, Agent, or Firm*—Burns, Doane, Swecker & Mathis, L.L.P.

[57] ABSTRACT

A novel nitroisourea derivative and a process for producing the same, which is an important intermediate for the production of a nitroguanidine derivative having an insecticidal activity, and a process for producing a nitroguanidine derivative having an insecticidal activity using the nitroisourea derivative. The process for producing a nitroguanidine derivative represented by formula (1), effective as an insecticide is shown by reaction scheme (2):

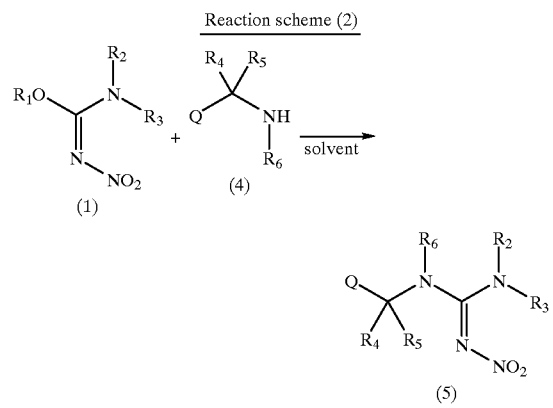

wherein $R_1$ represents an alkyl group having from 1 to 4 carbon atoms or a benzyl group; $R_2$ represents an alkyl group having from 1 to 4 carbon atoms; $R_3$, $R_4$, $R_5$ and $R_6$ each independently represents a hydrogen atom or an alkyl group having from 1 to 4 carbon atoms; and Q represents a 5-membered or 6-membered heterocyclic ring having at least one of the following: a nitrogen atom, an oxygen atom or a sulfur atom, one of the hydrogen atoms being substitutable with a halogen atom.

11 Claims, No Drawings

NITROISOUREA DERIVATIVE

FIELD OF THE INVENTION

The present invention relates to a novel nitroisourea derivative, a process for producing the same, and a process for producing a nitroguanidine derivative using the above nitroisourea derivative as an intermediate, having an insecticidal activity.

BACKGROUND OF THE INVENTION

A nitroguanidine derivative having an insecticidal activity and a process for producing the same are described in JP02288860A, JP03157308A and JP07179448A. However, for example in JP 07179448A, the problem occurs in the production process that exchange reactions between an isothiourea derivative and an amine are frequent thereby releasing a mercaptan as a by-product giving an offensive odor.

As an alternative process, JP10120666A discloses a process for producing a guanidine derivative represented by formula (B) having an insecticidal activity by reacting an isourea compound or a salt thereof represented by formula (A) with an amine or a salt thereof:

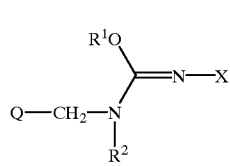

(A)

wherein $R^1$ represents a hydrocarbon group, which may have a substituent; $R^2$ represents a hydrogen atom or a hydrocarbon group, which may have a substituent; Q represents a heterocyclic group, which may have a substituent; and X represents an electron withdrawing group,

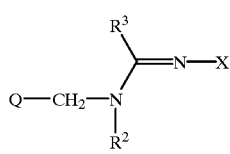

(B)

wherein $R^3$ represents an amino group, which may have a substituent; and $R^2$, Q, and X have the same meanings as above.

According to this process, however, there are problems in that the expensive isourea derivative represented by formula (A) must be used as an intermediate to produce the guanidine derivative represented by formula (B) having an insecticidal activity.

SUMMARY OF THE INVENTION

An object of the invention is to provide a novel nitroisourea derivative that overcomes the problems described above and is important as an intermediate for the production of a guanidine derivative having an insecticidal activity.

Another object of the invention is to provide a novel nitroisourea derivative that is inexpensive and useful as an intermediate for the production of not just one, but various guanidine derivatives having an insecticidal activity.

A further object of the invention is to provide a process for producing a nitroguanidine derivative having an insecticidal activity during which no mercaptan giving an offensive odor is produced.

A still further object of the invention is to provide a process for producing a nitroguanidine derivative having an insecticidal activity by using the above nitroisourea derivative.

As a result of intensive investigations by the inventors, a nitroisourea derivative that is different from the isourea compound represented by formula (A) described in JP10120666A has been found as an important intermediate for the production of a nitroguanidine derivative having an insecticidal activity, and it has been found that various nitroguanidine derivatives having an insecticidal activity can be easily produced by using the new nitroisourea derivative. And the present invention has been completed.

The invention relates to a nitroisourea derivative represented by formula (1):

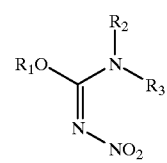

(1)

wherein $R_1$ represents an alkyl group having from 1 to 4 carbon atoms or a benzyl group; $R_2$ represents an alkyl group having from 1 to 4 carbon atoms; and $R_3$ represents a hydrogen atom or an alkyl group having from 1 to 4 carbon atoms.

The invention also relates to a process for producing the nitroisourea derivative represented by formula (1) above, the process comprising a step of reacting a nitroisourea represented by formula (2) with an amine or a salt thereof represented by formula (3) at pH of from 7.0 to 9.0:

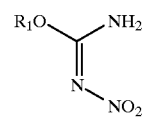

(2)

wherein $R_1$ has the same meaning as above,

(3)

wherein $R_2$ and $R_3$ have the same meanings as above.

The invention also relates to a process for producing a nitroguanidine derivative represented by formula (5):

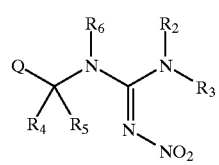

(5)

wherein $R_2$ and $R_3$ have the same meanings as above; $R_4$, $R_5$ and $R_6$ each independently represents a hydrogen atom or an alkyl group having from 1 to 4 carbon atoms; and Q represents a 5-membered or 6-membered heterocyclic ring having at least one of the following: a nitrogen atom, an oxygen atom or a sulfur atom, one of the hydrogen atoms being substitutable with a halogen atom, the process comprising a step of reacting the nitrosourea derivative represented by formula (1) with an amine derivative resented by formula (4):

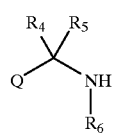

wherein $R_4$, $R_5$, $R_6$ and Q have the same meanings as above.

DETAILED DESCRIPTION OF THE INVENTION

The invention will be described in detail below.

In the invention, examples of alkyl groups having from 1 to 4 carbon atoms represented by $R_1$, $R_2$, $R_3$, $R_4$, $R_5$ and $R_6$ include a methyl group, an ethyl group, a n-propyl group, an i-propyl group, a n-butyl group, an i-butyl group and a t-butyl group. Examples of the 5-membered or 6-membered heterocyclic ring having at least one of the following: a nitrogen atom, an oxygen atom or a sulfur atom, one of the hydrogen atoms being substitutable with a halogen atom, include pyridyl group, a pyridazyl group, a pyrimidyl group, a pyrazolyl group, an imidazolyl group, a furanyl group, tetrahydrofuranyl group, an isoxazolyl group, an oxazolyl group, a thienyl group, a tetrahydrothienyl group, a thiazolyl group and an isothiazoyl group.

In the invention, $R_1$ and $R_2$ each independently preferably represents an alkyl group having from 1 to 4 carbon atoms; and $R_3$ preferably represents a hydrogen atom or an alkyl group having from 1 to 4 carbon atoms and more preferably a hydrogen atom. $R_4$, $R_5$, and $R_6$ each preferably represent a hydrogen atom. Q preferably represents a pyridyl group, which may be substituted with a halogen atom, a thiazolyl group, which may be substituted with a halogen atom, or a tetrahydrofuryl group. Among these, Q more preferably represents a 2-chloro-5-thiazolyl group, a 2-chloro-5-pyridinyl group or a 3-tetrahydorfuranyl group since these exhibit an excellent insecticidal activity.

The compound represented by formula (1) according to the invention is a novel compound and can be produced by the process shown by reaction scheme (1):

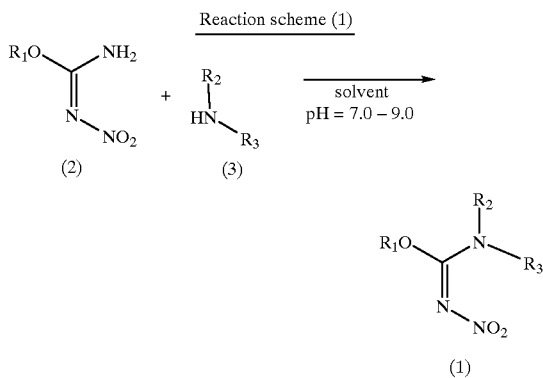

wherein $R_1$, $R_2$ and $R_3$ have the same meanings as above.

According to reaction scheme (1), the nitroisourea derivative represented by formula (1) can be produced by reacting the compound represented by formula (2) with a known amine or a salt thereof represented by formula (3) in a solvent, adjusting to have a pH of from 7.0 to 9.0, preferably a pH of from 7.0 to 8.0. When the pH is less than 7.0, the reaction scarcely proceeds at all, and when pH is more than 9.0, no target compound can be afforded.

Examples of an acid for forming a salt with the amine represented by formula (3) include a mineral acid such as hydrochloric acid, sulfuric acid or phosphoric acid; a sulfonic acid such as methanesulfonic acid or p-toluenesulfonic acid; and a carboxylic acid such as acetic acid or propionic acid.

Examples of the solvent used in the reaction shown by reaction scheme (1) include water; an alcohol such as methanol or ethanol; an aprotic polar solvent such as dimethylformamide (DMF), dimethylsulfoxide (DMSO) or 1,3-dimethyl-2-imidazolidinone (DMI); an ether such as tetrahydrofuran (THF) or dioxane; a nitrile such as acetonitrile and propionitrile; and a ketone such as acetone.

For the adjustment of the pH in the reaction shown by reaction scheme (1), a combination of an acid including a mineral acid such as hydrochloric acid, sulfuric acid or phosphoric acid, and a base including an alkali metal hydroxide such as sodium hydroxide or potassium hydroxide; and a buffer solution including a general buffer solution such as a sodium borate-hydrochloric acid buffer solution, and a special buffer solution such as a tris-hydrochloric acid buffer solution (tris(hydroxymethyl)aminomethane-hydrochloric acid buffer solution) and a triethanolamine-hydrochloric acid buffer solution, may be used.

The amount of the amine and a salt thereof represented by formula (3) is preferably from 1 to 2 equivalents, and more preferably from 1 to 1.1 equivalents, per 1 equivalent of the compound represented by formula (2).

The compound represented by formula (2) in reaction scheme (1) is a known compound and can be produced, for example, by nitration of 1-methylisourea sulfate as described in Recl. Trav. Chem. Pays-Bas, vol. 81, p. 69 (1962).

The reaction temperature and the reaction time of the reaction described above may change within a broad range. In general, the reaction temperature is preferably from −20 to 200° C., and more preferably from 0 to 100° C., and the reaction time is preferably from 0.01 to 50 hours, and more preferably from 0.1 to 15 hours.

In the case where $R_3$ of the nitroisourea derivative represented by formula (1) is a hydrogen atom, a tautomer thereof may be present in an arbitrary proportion as shown in the following scheme. The isomer and a mixture thereof are encompassed by the invention.

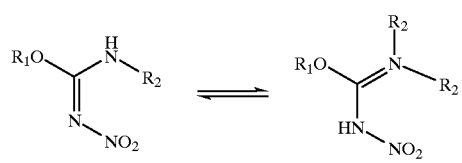

The nitroguanidine derivative represented by formula (5) having an insecticidal activity can be produced from the nitroisourea derivative represented by formula (1) through reaction scheme (2):

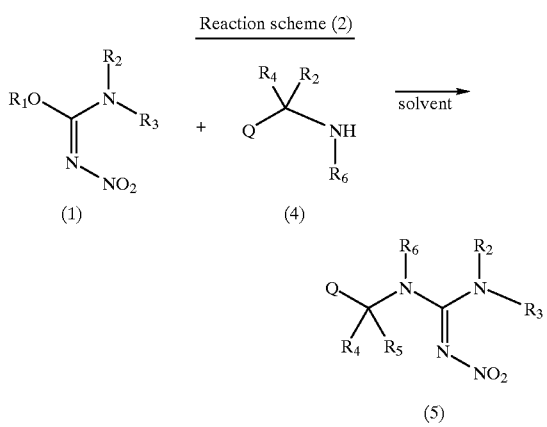

Reaction scheme (2)

wherein $R_2$, $R_3$, $R_4$, $R_5$, $R_6$ and Q have the same meanings as above.

According to reaction scheme (2), the nitroguanidine derivative represented by formula (5) having an insecticidal activity can be produced by reacting the nitroisourea derivative represented by formula (1) with the amine or a salt thereof represented by formula (4) in a solvent in the presence or absence of a base.

Examples of the base used in the reaction shown in reaction scheme (2) include an alkali metal hydroxide such as sodium hydroxide and potassium hydroxide; an alkaline earth metal hydroxide such as magnesium hydroxide and calcium hydroxide; an alkali metal hydride such as sodium hydride and potassium hydride; an alkali metal alcoholate such as sodium methoxide and sodium ethoxide; an alkaline metal oxide such as sodium oxide; an alkali metal carbonate such as potassium carbonate and sodium carbonate; an alkali metal phosphate such as potassium phosphate, sodium phosphate, dipotassium hydrogenphosphate and disodium hydrogenphosphate; an alkali metal acetate such as sodium acetate and potassium acetate; and an organic base such as pyridine, 4-(dimethylamino)pyridine, triethylamine and diazabicycloundecene (DBU).

Examples of the solvent used in the reaction shown by reaction scheme (2) include water; an alcohol such as methanol, ethanol, propanol and butanol; a halogenated hydrocarbon such as dichloromethane and chloroform; an aromatic hydrocarbon such as benzene, toluene and xylene; an aprotic polar solvent such as dimethylformamide (DMF), dimethylacetamide (DMA), dimethylsulfoxide (DMSO), 1,3-dimethyl-2-imidazolidinone (DMI) and 1-methyl-2-pyrrolidone (NMP); an ether such as ethyl ether, isopropyl ether, 1,2-dimethoxyethane, tetrahydrofuran (THF) and dioxane; a nitrile such as acetonitrile and propionitrile; and ketone such as acetone and isopropyl ketone. Among these, water and an alcohol are particularly preferred.

The amount of the amine represented by formula (4) is preferably from 1 to 2 equivalents, and more preferably from 1 to 1.2 equivalents, per 1 equivalent of the nitroisourea derivative represented by formula (1).

The reaction temperature and the reaction time of the reaction shown by reaction scheme (2) may change within a broad range. In general, the reaction temperature is preferably from −20 to 200° C., and more preferably from 0 to 100° C., and the reaction time is preferably from 0.01 to 50 hours, and more preferably from 0.1 to 15 hours.

The amine represented by formula (4) in reaction scheme (2) is a known compound and can be produced, for example, by methods described in DE3727126A, JP05286936A, JP0179448A, EP446913A and JP04021674A.

Examples of an acid forming a salt with the amine represented by formula (4) in reaction scheme (2) include a mineral acid, such as hydrochloric acid, sulfuric acid and phosphoric acid; a sulfonic acid, such as methanesulfonic acid and p-toluenesulfonic acid; and a carboxylic acid, such as acetic acid and propionic acid.

The nitroguanidine derivative, represented by formula (5), thus obtained exhibits an excellent insecticidal activity.

The invention will be specifically described below with reference to examples and reference examples, but the invention is not construed as being limited thereto.

EXAMPLE 1

Preparation of 1,3-dimethyl-2-nitroisourea (compound 1-1)

To a suspension of 1-methyl-2-nitroisourea (1.5 g) in water (15 ml), methylamine hydrochloride (0.9 g) was added (pH: 3.3). An aqueous sodium hydroxide (1%) was gradually added to maintain the pH of the suspension at 8 at room temperature. After the suspension was stirred for 3 hours at room temperature while maintaining the pH thereof to 8, an aqueous hydrochloric acid (4 M) was added, and then the solution was extracted with ethyl acetate. The organic layer was washed with water and dried over anhydrous magnesium sulfate, and it was then concentrated under reduced pressure. The residual oil was purified by silica gel column chromatography (hexane/ethyl acetate: 2/1) and then recrystallized (ethyl acetate-hexane), to obtain the desired compound (1.0 g) as colorless crystals.

$^1$H-NMR(CDCl$_3$, ppm): 3.02 (3H, d, J=4.9 Hz), 3.97 (3H, s) 9.10 (1H, s)

EXAMPLE 2

Preparation of 1,3-dimethyl-2-nitroisourea (compound 1-1)

To a suspension of 1-methyl-2-nitroisourea (1.0 g) in a buffer solution of a tris(hydroxymethyl) aminomethanehydrochloric acid (tris-hydrochloric acid buffer solution, 1.0 M, pH: 7.5, 10 ml), methylamine hydrochloride (0.6 g) was added at room temperature. After stirring for 3 hours, an aqueous hydrochloric acid (4 M) was added, and then the solution was extracted with ethyl acetate. The organic layer was washed with water and dried over anhydrous magnesium sulfate, and it was then concentrated under reduced pressure. The residual oil was purified with silica gel column chromatography (hexane/ethyl acetate: 2/1) and then recrystallized (ethyl acetate-hexane), to obtain the desired compound (0.8 g) as colorless crystals.

COMPARATIVE EXAMPLE 1

To a suspension of 1-methyl-2-nitroisourea (1.0 g) in water (10 ml), methylamine hydrochloride (0.6 g) was added (pH: 3.3). An aqueous sodium hydroxide (1%) was gradually added to maintain the pH of the suspension to 6.5 at room temperature. The suspension was stirred at room temperature while maintaining the pH thereof to 6.5, but the reaction did not proceed at all.

COMPARATIVE EXAMPLE 2

To a suspension of 1-methyl-2-nitroisourea (1.0 g) in water (10 ml), methylamine hydrochloride (0.6 g) was added (pH: 3.3). An aqueous sodium hydroxide (1%) was gradually added to maintain the pH of the suspension to 6.9 at room temperature. The suspension was stirred at room temperature while maintaining the pH thereof to 6.9, but the reaction did not proceed, and the desired compound was not obtained.

COMPARATIVE EXAMPLE 3

To a suspension of 1-methyl-2-nitroisourea (1.0 g) in water (10 ml), methylamine hydrochloride (0.6 g) was added (pH: 3.3). An aqueous sodium hydroxide (1%) was gradually added to maintain the pH of the suspension to 9.1 at room temperature. The suspension was stirred for 3 hours at room temperature while maintaining the pH thereof to 9.1. The reaction mixture was extracted with dichloromethane, and the organic layer was dried over anhydrous magnesium sulfate. An oily product obtained by concentrating the organic layer under reduced pressure was purified by silica gel column chromatography (hexane/ethyl acetate: 2/1) and then recrystallized (ethyl acetate-hexane) The desired compound was not obtained, but rather 1-methyl-2-nitroguanidine (0.9 g) was obtained as colorless crystals.

Compounds that can be produced in the same manner as in Examples 1 and 2 are shown in Table 1 below. In Table 1, Me represents a methyl group, Et represents an ethyl group, n-Pr represents a n-propyl group, i-Pr represents an isopropyl group, n-Bu represents a n-butyl group, and Bn represents a benzyl group.

TABLE 1

| Compound No. | $R_1$ | $R_2$ | $R_3$ |
| --- | --- | --- | --- |
| 1-1 | Me | Me | H |
| 1-2 | Et | Me | H |
| 1-3 | n-Pr | Me | H |
| 1-4 | i-Pr | Me | Me |
| 1-5 | n-Bu | Me | Me |
| 1-6 | Bn | Et | Me |
| 1-7 | Me | Et | H |
| 1-8 | Et | n-Pr | H |
| 1-9 | Me | n-Pr | H |
| 1-10 | Et | i-Pr | H |
| 1-11 | Me | i-Pr | H |
| 1-12 | Et | n-Bu | H |
| 1-13 | Me | n-Bu | H |
| 1-14 | Et | Me | Me |
| 1-15 | Me | Me | Me |
| 1-16 | Et | Me | Me |

EXAMPLE 3

Preparation of 1-[(2-chloro-5-pyridyl)methyl]-3-methyl-2-nitroguanidine (compound 2-1)

To a solution of 1,3-dimethyl-2-nitroisourea (1.0 g) in methanol (10 ml), [(2-chloro-5-pyridyl)methyl]amine (1.28 g) was added, and the mixture was stirred for 5 hours at room temperature. An oily product obtained by concentrating the reaction mixture under reduced pressure was purified by silica gel column chromatography (ethyl acetate) and then recrystallized (methanol-ether), to obtain the desired compound (1.40 g) as colorless crystals.

$^1$H-NMR(CDCl$_3$, ppm): 2.83 (3H, br-s), 4.42 (2H, br-s), 7.48 (1H, d, J=8.1 Hz), 7.78 (1H, dd, J=2.2 Hz, 8.1 Hz), 7.92 (1H, br-s), 8.35 (1H, d, J=2.2 Hz), 9.14 (1H, br-s)

EXAMPLE 4

Preparation of 1-[(2-chloro-5-thiazolyl)methyl]-3-methyl-2-nitroguanidine (compound 2-2)

To a solution of 1,3-dimethyl-2-nitroisourea (1.0 g) in methanol (10 ml), [(2-chloro-5-thiazolyl)methyl]amine (1.32 g) was added, and the mixture was stirred for 4 hours at room temperature. An oily product obtained by concentrating the reaction mixture under reduced pressure was purified with silica gel column chromatography (ethyl acetate) and then recrystallized (methanol-ether), to obtain the desired compound (1.11 g) as light yellow crystals.

$^1$H-NMR(CDCl$_3$, ppm): 2.80 (3H, br-s), 4.49 (2H, br-s), 7.58 (1H, s), 7.93 (1H, br-s), 9.31 (1H, br-s)

EXAMPLE 5

Preparation of 1-methyl-2-nitro-3-[(3-tetrahydrofuryl)methyl]-guanidine (compound 2-3)

To a solution of 1,3-dimethyl-2-nitroisourea (1.0 g) in methanol (10 ml), [(3-tetrahydrofuryl)methyl]amine (0.91 g) was added, and the mixture was stirred for 3 hours at room temperature. An oily product obtained by concentrating the reaction mixture under reduced pressure was purified by silica gel column chromatography (ethyl acetate) and then recrystallized (methanol-ether), to obtain the desired compound (1.44 g) as colorless crystals.

$^1$H-NMR(CDCl$_3$, ppm): 1.62–1.71 (1H, m), 2.05–2.16 (1H, m), 2.58–2.67 (1H, m),2.97 (3H, d, J=5.3 Hz), 3.36 (2H, br-t), 3.62–3.66 (1H, m), 3.71–3.84 (2H, m), 3.89–3.95 (1H, m), 6.04 (1H, br-s), 9.35 (1H, br-s)

EXAMPLE 6

Preparation of 1-[(2-chloro-5-pyridyl)methyl]-3-methyl-2-nitroguanidine (compound 2-1)

To a suspension of 1,3-dimethyl-2-nitroisourea (1.0 g) in water (10 ml), [(2-chloro-5-pyridyl)methyl]amine (1.28 g) was added, and the mixture was stirred for 3 hours at room temperature. The reaction mixture was diluted with water and then extracted with dichloromethane. The organic layer was dried over anhydrous magnesium sulfate and then concentrated under reduced pressure. The residual oil was purified by silica gel column chromatography (ethyl acetate) and then recrystallized (methanol-ether), to obtain the desired compound (1.23 g) as colorless crystals.

EXAMPLE 7

Preparation of 1-[(2-chloro-5-thiazolyl)methyl]-3-methyl-2-nitroguanidine (compound 2-2)

To a suspension of 1,3-dimethyl-2-nitroisourea (1.0 g) in water (10 ml), [(2-chloro-5-thiazolyl)methyl]amine (1.32 g) was added, and the mixture was stirred for 5 hours at room temperature. The reaction mixture was diluted with water and then extracted with dichloromethane. The organic layer was dried over anhydrous magnesium sulfate and then concentrated under reduced pressure. The residual oil was purified by silica gel column chromatography (ethyl acetate) and then recrystallized (methanol-ether), to obtain the desired compound (0.95 g) as light yellow crystals.

EXAMPLE 8

Preparation of 1-methyl-2-nitro-3-[(3-tetrahydrofuryl)methyl]-guanidine (compound 2-3)

To a suspension of 1,3-dimethyl-2-nitroisourea (1.0 g) in water (10 ml), [(3-tetrahydrofuryl)methyl]amine (0.91 g) was added, and the mixture was stirred for 4 hours at room temperature. The reaction mixture was diluted with water and then extracted with dichloromethane. The organic layer was dried over anhydrous magnesium sulfate and then concentrated under reduced pressure. The residual oil was purified by silica gel column chromatography (ethyl acetate) and then recrystallized (methanol-ether), to obtain the desired compound (1.24 g) as colorless crystals.

Compounds that can be produced in the same manner as in Examples 3 to 8 are shown in Table 2 below. In Table 2, Me represents a methyl group, Et represents an ethyl group, n-Pr represents a n-propyl group, i-Pr represents an isopropyl group, and n-Bu represents a n-butyl group.

TABLE 2

| Compound No. | $R_1$ | $R_2$ | $R_3$ | $R_4$ | $R_5$ | $R_6$ | Q |
|---|---|---|---|---|---|---|---|
| 2-1  | Me | Me   | H  | H  | H  | H  | 2-chloro-5-pyridyl |
| 2-2  | Me | Me   | H  | H  | H  | H  | 2-chloro-5-thiazolyl |
| 2-3  | Me | Me   | H  | H  | H  | H  | 3-tetrahydrofuryl |
| 2-4  | Me | Me   | Me | H  | H  | H  | 2-chloro-5-pyridyl |
| 2-5  | Me | Me   | Me | H  | H  | H  | 2-chloro-5-thiazolyl |
| 2-6  | Me | Me   | Me | H  | H  | H  | 3-tetrahydrofuryl |
| 2-7  | Me | Et   | H  | H  | H  | H  | 2-chloro-5-pyridyl |
| 2-8  | Me | Et   | H  | H  | H  | H  | 2-chloro-5-thiazolyl |
| 2-9  | Me | Et   | H  | H  | H  | H  | 3-tetrahydrofuryl |
| 2-10 | Me | n-Pr | H  | H  | H  | H  | 2-chloro-5-pyridyl |
| 2-11 | Me | n-Pr | H  | H  | H  | H  | 2-chloro-5-thiazolyl |
| 2-12 | Me | n-Pr | H  | H  | H  | H  | 3-tetrahydrofuryl |
| 2-13 | Me | i-Pr | H  | H  | H  | H  | 2-chloro-5-pyridyl |
| 2-14 | Me | i-Pr | H  | H  | H  | H  | 2-chloro-5-thiazolyl |
| 2-15 | Me | i-Pr | H  | H  | H  | H  | 3-tetrahydrofuryl |
| 2-16 | Me | n-Bu | H  | H  | H  | H  | 2-chloro-5-pyridyl |
| 2-17 | Me | n-Bu | H  | H  | H  | H  | 2-chloro-5-thiazolyl |
| 2-18 | Me | n-Bu | H  | H  | H  | H  | 3-tetrahydrofuryl |
| 2-19 | Me | Me   | H  | Me | H  | H  | 2-chloro-5-pyridyl |
| 2-20 | Me | Me   | H  | Me | H  | H  | 2-chloro-5-thiazolyl |
| 2-21 | Me | Me   | H  | Me | H  | H  | 3-tetrahydrofuryl |
| 2-22 | Me | Me   | H  | Me | Me | H  | 2-chloro-5-pyridyl |
| 2-23 | Me | Me   | H  | Me | Me | H  | 2-chloro-5-thiazolyl |
| 2-24 | Me | Me   | H  | Me | Me | H  | 3-tetrahydrofuryl |
| 2-25 | Me | Me   | H  | H  | H  | Me | 2-chloro-5-pyridyl |
| 2-26 | Me | Me   | H  | H  | H  | Me | 2-chloro-5-thiazolyl |
| 2-27 | Me | Me   | H  | H  | H  | Me | 3-tetrahydrofuryl |

The compound represented by formula (1) according to the invention is a novel compound, and furthermore, various nitroguanidine derivatives having an insecticidal activity can be easily produced by the reaction of the compound and an amine represented by formula (4) without by-producing a mercaptan giving an offensive odor. Therefore, the compound represented by formula (1) according to the invention can be used as an important intermediate for the production of a guanidine derivative having an insecticidal activity.

What is claimed is:

1. A nitroisourea derivative represented by formula (1):

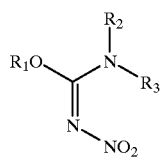

wherein $R_1$ represents an alkyl group having from 1 to 4 carbon atoms or a benzyl group; $R_2$ represents an alkyl group having from 1 to 4 carbon atoms; and $R_3$ represents a hydrogen atom or an alkyl group having from 1 to 4 carbon atoms.

2. The nitroisourea derivative according to claim 1, wherein $R_1$ and $R_2$ each independently represents an alkyl group having from 1 to 4 carbon atoms; and $R_3$ represents a hydrogen atom or an alkyl group having from 1 to 4 carbon atoms.

3. The nitroisourea derivative according to claim 2, wherein $R_3$ represents a hydrogen atom.

4. A process for producing a nitroisourea derivative represented by formula (1):

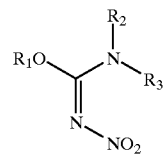

wherein $R_1$ represents an alkyl group having from 1 to 4 carbon atoms or a benzyl group; $R_2$ represents an alkyl group having from 1 to 4 carbon atoms; and $R_3$ represents a hydrogen atom or an alkyl group having from 1 to 4 carbon atoms, said process comprising a step of reacting a nitroisourea represented by formula (2) with an amine or a salt thereof represented by formula (3) at pH of from 7.0 to 9.0:

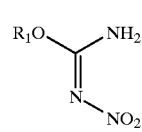

wherein $R_1$ has the same meaning as above and wherein $R_2$ and $R_3$ have the same meanings as above

5. The process for producing a nitroisourea derivative according to claim 4, wherein $R_1$ and $R_2$ each independently represents an alkyl group having from 1 to 4 carbon atoms; and $R_3$ represents a hydrogen atom or an alkyl group having from 1 to 4 carbon atoms.

6. The process for producing a nitroisourea derivative according to claim 5, wherein $R_3$ represents a hydrogen atom.

7. A process for producing a nitroguanidine derivative represented by formula (5):

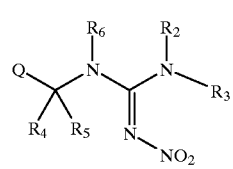

wherein $R_2$ represents an alkyl group having from 1 to 4 carbon atoms; $R_3$, $R_4$, $R_5$ and $R_6$ each independently represent a hydrogen atom or an alkyl group having from 1 to 4 carbon atoms; and Q represents a 5-membered or 6-membered heterocyclic ring having at least one of the following: a nitrogen atom, an oxygen atom or a sulfur atom, and being unsubstituted or being substituted with a halogen atom, said process comprising a step of reacting a nitroisourea derivative represented by formula (1) with an amine derivative represented by formula (4):

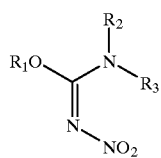

(1)

wherein $R_1$ represents an alkyl group having from 1 to 4 carbon atoms or a benzyl group; and $R_2$ and $R_3$ have the same meanings as above,

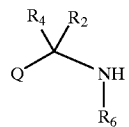

(4)

wherein $R_4$, $R_5$, $R_6$ and Q have the same meanings as above.

8. The process for producing a nitroguanidine derivative according to claim 7, wherein $R_1$ and $R_2$ each represents an alkyl group having from 1 to 4 carbon atoms; $R_3$, $R_4$, $R_5$ and $R_6$ each independently represents a hydrogen atom or an alkyl group having from 1 to 4 carbon atoms; and Q represents a pyridyl group, which may be substituted with a halogen atom, a thiazolyl group, which may be substituted with a halogen atom, or a tetrahydrofuryl group.

9. The process for producing a nitroguanidine derivative according to claim 8, wherein $R_1$ and $R_2$ each represents a methyl group; $R_3$, $R_4$, $R_5$, and $R_6$ each represents a hydrogen atom; and Q represents a pyridyl group, which may be substituted with a halogen atom.

10. The process for producing a nitroguanidine derivative according to claim 8, wherein $R_1$ and $R_2$ each represents a methyl group; $R_3$, $R_4$, $R_5$, and $R_6$ each represents a hydrogen atom; and Q represents a thiazolyl group, which may be substituted with a halogen atom.

11. The process for producing a nitroguanidine derivative according to claim 8, wherein $R_1$ and $R_2$ each represents a methyl group; $R_3$, $R_4$, $R_5$, and $R_6$ each represents a hydrogen atom; and Q represents a tetrahydrofuryl group.

* * * * *

UNITED STATES PATENT AND TRADEMARK OFFICE
CERTIFICATE OF CORRECTION

PATENT NO. : 6,124,466  
DATED : September 26, 2000  
INVENTOR(S) : Hirozumi Matsuno et al.

It is certified that error appears in the above-identified patent and that said Letters Patent is hereby corrected as shown below:

Column 11,
Line 16, change "$R_2$" to -- $R_5$ --

Signed and Sealed this

Second Day of April, 2002

Attest:

*Attesting Officer*

JAMES E. ROGAN  
*Director of the United States Patent and Trademark Office*